United States Patent [19]

Sorenson et al.

[11] 4,033,345
[45] July 5, 1977

[54] AUTOLOGOUS TRANSFUSION FILTER SYSTEM AND METHOD

[75] Inventors: James L. Sorenson; Karl A. Pannier, Jr., both of Salt Lake City; Gordon S. Reynolds, Bountiful, all of Utah

[73] Assignee: Sorenson Research Co., Inc., Salt Lake City, Utah

[22] Filed: Jan. 21, 1976

[21] Appl. No.: 651,376

Related U.S. Application Data

[63] Continuation-in-part of Ser. No. 631,584, Nov. 13, 1975, which is a continuation-in-part of Ser. No. 580,087, May 22, 1975.

[52] U.S. Cl. .............. 128/214 R; 128/214 F; 128/276; 137/205
[51] Int. Cl.² .............. A61M 1/02; A61M 5/14
[58] Field of Search ........ 128/214 R, 214 F, 214.2, 128/276–278; 137/205

[56] References Cited

UNITED STATES PATENTS

| 2,409,734 | 10/1946 | Bucher | 128/214 F |
| 3,054,401 | 9/1962 | Gewecke | 128/214 F |
| 3,191,600 | 6/1965 | Everett | 128/276 |
| 3,492,991 | 2/1970 | Dyer | 128/214 R |
| 3,680,560 | 8/1972 | Pannier et al. | 128/276 |
| 3,866,608 | 2/1975 | Reynolds et al. | 128/276 |
| 3,896,733 | 7/1975 | Rosenberg | 128/214 R |

FOREIGN PATENTS OR APPLICATIONS

| 822,195 | 10/1959 | United Kingdom | 128/214 C |

Primary Examiner—Dalton L. Truluck
Attorney, Agent, or Firm—H. Ross Workman; J. Winslow Young

[57] ABSTRACT

An autologous blood transfusion system having at least two interconnected blood receptacles and an associated filter assembly, the first receptacle being evacuated and connected to a suction device for aspirating blood. The second receptacle takes blood from the first by overcoming the vacuum in the first with a greater vacuum in the second without interrupting the ability of the suction device to simultaneously aspirate blood. The second receptacle may comprise a transfer bag for reinfusion into the patient or an infusion set may be connected to the second receptacle to permit simultaneous collection of the blood from the patient and infusion of the blood back into the patient. In either case, the second receptacle is selectively exposed to positive pressure to force blood through the filter assembly and expel the blood from the second receptacle into the transfer bag or patient. The method includes aspirating blood from the patient and collecting blood in the first receptacle. Blood is thereafter transferred to the second receptacle by increasing the vacuum in the second receptacle over the first receptacle without interrupting the ability of the suction device to simultaneously aspirate blood. Blood is then filtered by subjecting the blood within the second receptacle to positive fluid pressure which urges the blood through the filter assembly.

12 Claims, 7 Drawing Figures

AUTOLOGOUS TRANSFUSION FILTER SYSTEM AND METHOD

RELATED APPLICATION

This application is a continuation-in-part of copending U.S. Pat. application Ser. No. 631,584, filed Nov. 13, 1975, which is, in turn, a continuation-in-part of copending U.S. Pat. application Ser. No. 580,087, filed May 22, 1975.

BACKGROUND

1. Field of the Invention

The invention relates to system and methods for autologous blood transfusion and more particularly to a filtration system and method for autologous blood transfusion.

2. The Prior Art

Homologous blood transfusion is the well-known technique of collecting blood from a donor and thereafter storing the blood for later infusion into another patient. For many years, homologous blood transfusion has been the standard technique for replacing a patient's blood after surgery, obstetrical complications, traumatic hemorrhage and the like.

Homologous blood transfusion has evidenced a number of serious complications. For example, frequently elective surgical procedures must be postponed because of the unavailability of compatible homologous blood. In smaller towns and cities, there is frequently a lack of qualified donors. Also in larger metropolitan areas, there is a great need for quantities of blood to cover trauma situations and the increasing number of elective major surgical procedures. It is well-known that homologous blood must be cross matched to ascertain compatibility before the homologous blood is administered to a patient. Cross matching is an expensive and time consuming procedure and is not always effective in detecting blood incompatibility.

At present, the most serious complication due to homologous blood transfusion is post-transfusion hepatitis. The National Heart and Lung Institute has reported hundreds of deaths and thousands of cases of incapacitating illness resulting from post-transfusion hepatitis. Other complications, well-known in homologous blood transfusion, include isoimmunization, transmission of disease, incompatibility, hemolytic reactions and over transfusion.

These problems are substantially circumvented through the technique of autologous blood transfusion. Autologous transfusion is defined as the reinfusion of the patient's own blood. The desirability of autologous transfusion has been acknowledged for many years. Structure accommodating autologous transfusion is disclosed in applicant's U.S. Pat. No. 3,866,608 and in U.S. Pat. No. 3,896,733. Autologous blood transfusion may, however, pose undesirable risks to the patient if the blood is contaminated or carries undesirable particulate matter. For example, a patient may suffer serious thoractic and/or abdominal hemorrhage from traumatic injury wherein the blood may be contaminated with bile, fecal matter or the like. Even in surgical procedures undesirable fat particles and tissue are carried with the blood into the collection system. Until this present invention, however, no structure and method has been known which would accommodate effective filtration of a patient's blood for reinfusion without interrupting the ability to simultaneously collect the blood.

BRIEF SUMMARY AND OBJECTS OF THE INVENTION

The present invention comprises novel system and method for collecting a patient's blood in a first receptacle and implementing variable fluid pressure for forcibly transferring the patient's blood through a filter assembly prior to reinfusing the patient from a second receptacle, all without interrupting the collection process in the first receptacle.

It is, therefore, a primary object of the present invention to provide improvements in autologous blood transfusion.

It is another object of the present invention to provide an improved extracorporeal blood circuit presenting a filter for removing undesirable blood constituents prior to reinfusion.

One still further object of the present invention is to provide an autologous blood system and method for pressure-forcing blood through a filter prior to reinfusion of the blood.

One still further valuable object of the present invention is to provide structure and method accommodating interchange of filter assemblies.

Another important object of the invention is to provide structure and methods for removing predetermined blood contaminants by selective filtration.

These and other objects and features of the present invention will become more fully apparent from the following description and appended claims taken in conjunction with the accompanying drawing.

DETAILED DESCRIPTION OF THE PREFERRED EMBODIMENTS

The Apparatus

Figure 1:
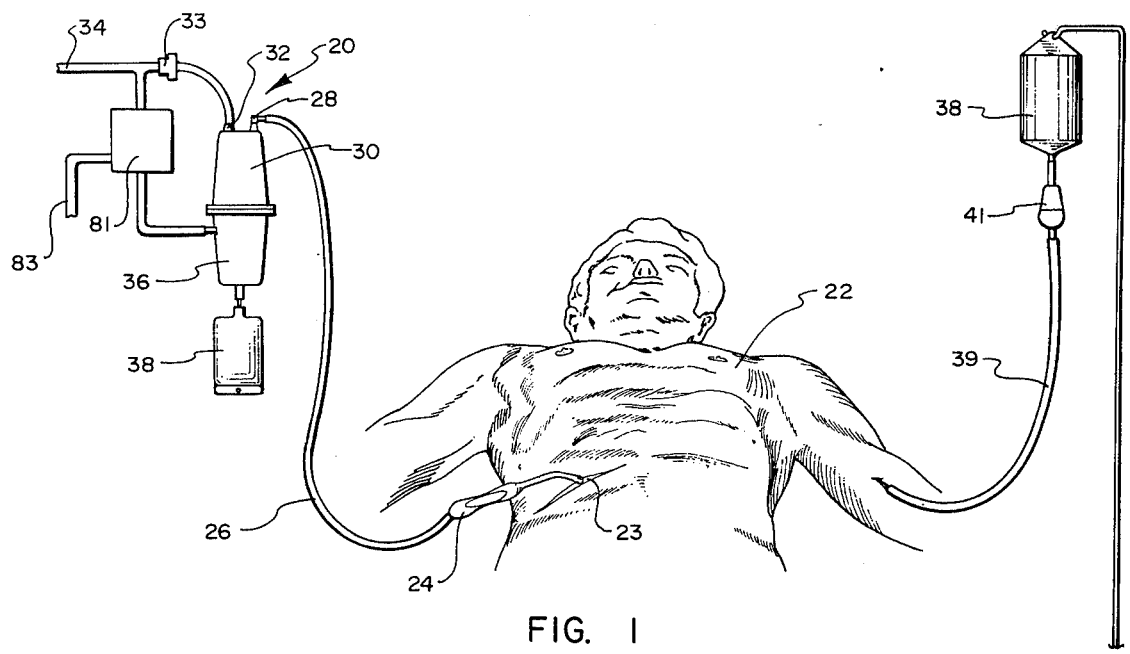
FIG. 1 is a schematic representation of one preferred embodiment of the invention illustrating structure and method for simultaneously collecting and infusing a patient's blood incorporating the embodiments of FIGS. 2–6.

Attention is now directed to the drawing wherein like numerals represent like parts throughout. Referring generally to FIG. 1, the autologous blood transfusion system generally designated 20 is schematically illustrated. The purpose for the autologous system 20 is to recover and reinfuse the blood of a patient 22. Normally, the source of blood from the patient will be through a wound or surgical incision represented at 23. Commonly, autologous blood transfusion has its greatest value under circumstances where great amounts of blood would normally be lost in a short period of time from the patient. A number of vascular, thoracic and abdominal surgeries could come within this category. Another significant area deals with hemorrhagic trauma resulting from injury to the patient. In either event, blood can normally be collected near the hemorrhage site.

It is presently preferred that the blood be collected with an aspiration wand 24 as is conventional. The aspiration wand 24 is connected by an elongated tube 26 to the inlet port 28 of a first receptacle 30. The first receptacle 30 has a vacuum port 32 conventionally connected to a vacuum line 34 which communicates with a conventional vacuum source (not shown) through a conventional pressure reducer 33.

The first receptacle 30 is evacuated through the vacuum line 34 so as to create a suction in the aspiration wand 24 and tube 26. Thus, blood is aspirated at the wand 24 and deposited in the first receptacle 30. It is presently preferred that the aspiration wand 24 be provided with the capability of mixing anticoagulant with the aspirated blood as disclosed in copending application Ser. No. 555,008 filed Mar. 3, 1975.

After the blood has been collected in the first receptacle, it must be communicated to a second receptacle 36. It is apparent by reference to FIG. 1 that without some force being exerted upon the blood, the blood will not move out of the first receptacle 30 into the second receptacle 36. Failure of the blood to naturally transfer into the second receptacle results because there is a significant negative pressure within the first receptacle, normally on the order of magnitude of 30 millimeters of mercury (mm Hg). Further, when the second receptacle is coupled directly to a flexible tranfer bag 38, atmospheric pressure will discourage blood flow into the second receptacle 36. Structure must be provided, therefore, which will facilitate transfer of blood from the first receptacle 30 to the second receptacle 36.

Figure 2:
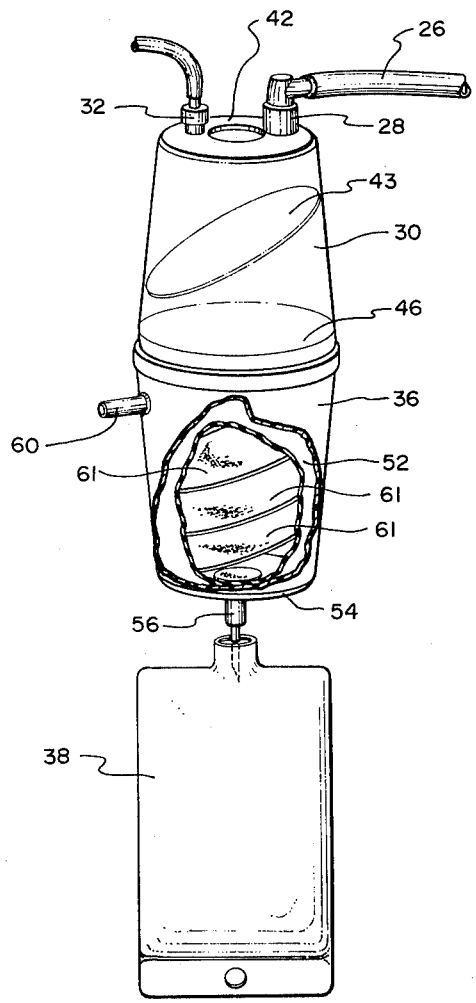
FIG. 2 is a schematic perspective illustration of a presently preferred collection system embodiment with portions broken away to reveal a filter assembly within the second receptacle.

Referring now particularly to FIG. 2, the first receptacle 30 is illustrated as a rigid, transparent plastic container. The top or cap 42 of the container is provided with diametrally opposed ports 28 and 32. The port 32 is connected through the vacuum line 34 (see FIG. 1) to a vacuum source (not shown). The inlet port 28, as described above, is connected to the tube 26 (see FIG. 1). Blood passing through the tube 26 enters the interior of the first receptacle 30 at the port 28.

Figure 3:
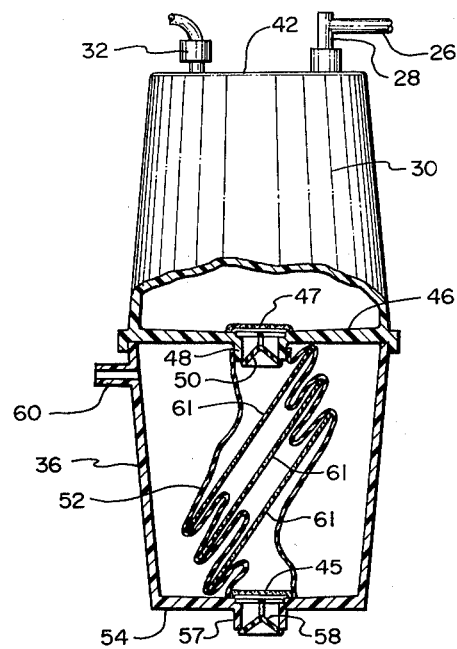
FIG. 3 is a schematic fragmentary cross-sectional view of the embodiment of FIG. 2 as the liner of second receptacle is being collapsed under pressure.

As illustrated in FIGS. 2 and 3 the first receptacle 30 has a rigid bottom 46 which may taper conically downward and carries a depending boss 48. The boss 48 confines a unidirectional valve 50. Thus, blood collected in the receptacle 30 will pool at the bottom 46 toward the center thereof at the location of the valve 50. Preferably, a screen filter 47 is mounted upon the bottom 46 immediately above the valve 50 to prevent the valve 50 from becoming obstructed with clots and other particulate matter in the blood.

The second receptacle 36 is located downstream from the receptacle 30 and may be unitary with the first receptacle 30, as shown in FIG. 2. The second receptacle 36 in the embodiment of FIGS. 1 and 2 is a rigid plastic container which substantailly circumscribes a flexible liner 52. The flexible liner 52 may be secured in any desirable way to the interior of the second receptacle 36, direct attachment to the boss 48 being illustrated in FIG. 3. It should be noted that the liner is attached to the boss 48 such that the interior of the first receptacle 30 communicates with the interior of the liner 52 through the valve 50. A depending boss 57 (FIG. 3), preferably having a valve 58 therein, is mounted upon the bottom 54 of receptacle 36. If desired, a spike 56 may be secured to the boss 57 (e.g. as shown in FIG. 2) to facilitate penetration of the transfer bag 38. The hollow liner 52 opens into the boss 57 so that the contents of the liner 52 can be expelled through the spike 56 as will be subsequently more fully described. The valve 58 may be an automatic one-way valve of conventional construction.

The liner 52 has a plurality of spaced filter elements 61 mounted within the liner 52 so as to form a filter assembly. While a single filter element 61 may be adequate, an array of elements is presently preferred to minimize particulate contamination of the blood. Each filter element is sealed at its peripheral mounting within the liner 52 so that all blood passing through liner 52 traverses each filter elements 61.

Filter elements 61 are less flexible than the liner 52. Accordingly, each filter element 61 is canted as shown in FIG. 2 when the liner is inflated. The array of filter elements is canted at an even greater angle when the liner 52 is collapsed as shown in FIG. 3 and as will be hereinafter more fully described.

The second receptacle 36 is provided with at least one fluid pressure port 60 which communicates with the interior of the receptacle 36 between the receptacle 36 and the liner 52. The second receptacle 36 may be evacuated through the fluid pressure port 60 or, alternatively, a positive pressure, preferably greater than atmospheric pressure may be exerted between the liner 52 and the receptacle 36 through the port 60. Positive pressure may be delivered from a conventional source 83 through a suitable three way valve 81 (see FIGS. 1 and 7).

The flow of blood between receptacle 30 and liner 52 is controlled in part by check valve 50 mounted between the first and second receptacles, the check valve 50 being of conventional well-known construction. An example of a suitable check valve is found in U.S. Pat. No. 3,742,952. The check valve is constructed to limit the flow of blood unidirectionally from the first receptacle 30 to the liner 52 within second receptacle 36 and to prevent retrograde flow. The valve 58 may be similar to that of valve 50.

The second receptacle 36 may be connected to a blood storage container 38 as shown in FIG. 2. The container 38 may be a plastic blood transfer bag or other suitable container for maintaining and storing blood. In this FIG. 2 embodiment, the second receptacle 36 and liner 52 cooperate to (a) overcome the negative pressure in receptacle 30 so as to transfer the blood into liner 52 without interrupting the negative pressure in receptacle 30 and (b) transfer the blood in liner 52 to the transfer bag 38 while continuing to collect blood in the first receptacle 30. The transfer bag 38 is filled by collapsing the liner 52 so as to force the blood through filter elements 61 and thereafter expel blood unidirectionally from the second receptacle 36 into the transfer bag 38. The transfer bag 38 is removably attached to the spike 56 at the self-sealing puncture site 61 of bag 38 so that the blood in transfer bag 38 can be reinfused into the patient as shown in FIG. 1. Notably detachment of the transfer bag 38 from the second receptacle 36 will not adversely interrupt the collection of blood in the first receptacle 30. In transfusing a patient's own blood from transfer bag 38, the bag 38 is connected to an infusion set 39 as shown in FIG. 1. The infusion set conventionally includes a bubble trap 41 and an infusion assembly 39.

Figure 7:
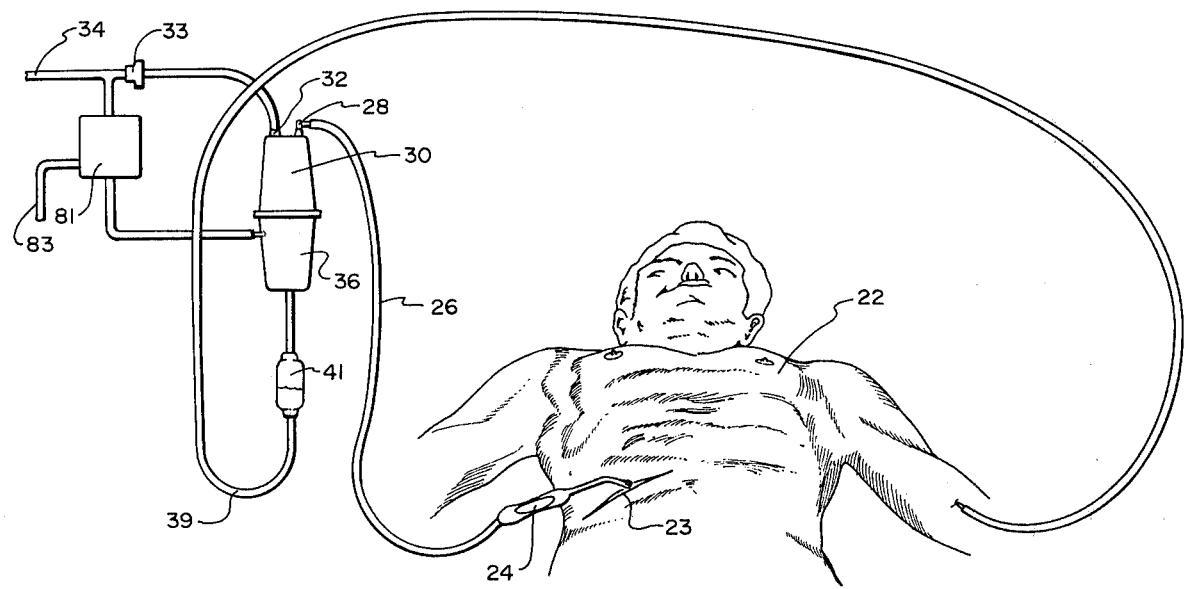
FIG. 7 is a schematic representation of still another presently preferred system and method embodiment of the invention for simultaneously collecting and infusing blood into a patient.

The embodiment of FIG. 7 is preferred when it is desired to infuse blood into the patient immediately upon collection of the blood.

In the operation of the embodiments of FIGS. 2 and 3, blood is received through the tube 26 into the first receptacle 30. A filter 43 will strain large tissue masses and bone fragments from the incoming blood. The blood will then pool at the bottom 46, the valve 50 being closed due to the negative pressure within the first receptacle 30.

As desired, a vacuum may be imposed at the port 60. Upon evacuation, the liner 52 will move from its initially collapsed position (see FIG. 3) to the inflated position illustrated in FIG. 2. Inasmuch as the vacuum imposed at the port 60 is greater than the vacuum imposed within the interior of the receptacle 30, the unidirectional valve 50 will open permitting blood to move from the first to the second receptacle. Within the second receptacle, the blood will pass through filter elements 61. Thereafter, positive fluid pressure is communicated through the port 60 between the liner 52 and the receptacle 36. Accordingly, the liner will commence to collapse as shown in FIG. 3 causing the unidirectional valve 50 to close and valve 58 to open. The contents of the liner 52 are thus urged into the transfer bag 38 in accordance with the embodiment of FIG. 1 or directly back into the patient in accordance with the embodiment of FIG. 7. It is observed that because the natural position of the filter elements 61 is canted (see FIG. 2) collapse of the liner 52 is permitted as the filter elements 61 shift to a more acute angular position as shown in FIG. 3. As the liner 52 is collapsed around the filter elements 61, blood is positively displaced through the filter elements.

Figure 4:
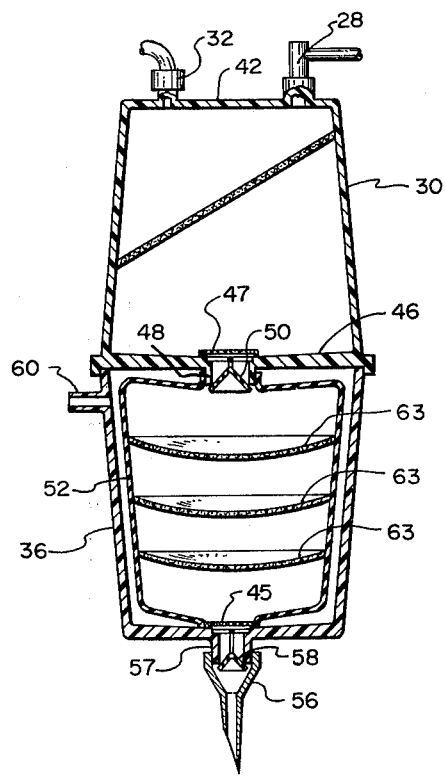
FIG. 4 illustrates in cross-section an alternative filter assembly embodiment mounted within a blood collection receptacle.
Figure 5:
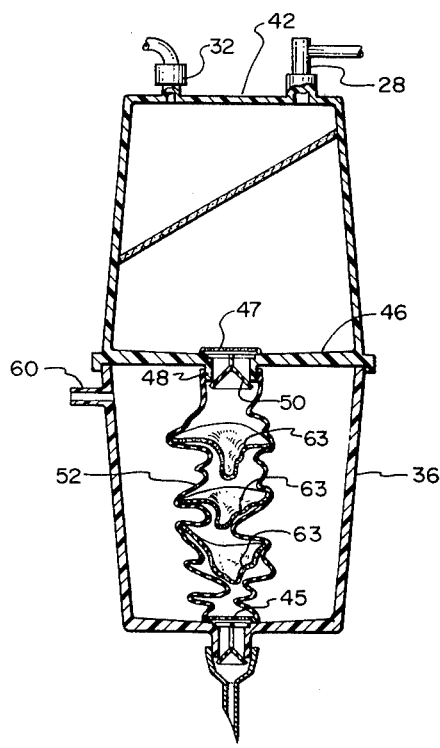
FIG. 5 is a cross-sectional illustration of the embodiment of FIG. 4 as the liner of the second receptacle is being collapsed under pressure.

The embodiment of FIGS. 4 and 5 is substantially the same as the embodiment of FIGS. 2 and 3 except that in the embodiments of FIGS. 4 and 5 the filter units 63 are highly flexible filters, preferably working upon the principle of particle attraction. The flexible filter units 63 may be oriented essentially horizontally when the receptacle 36 is in the position illustrated in FIG. 4 and when the liner 52 is inflated. When pressure is communicated through the port 60 between the receptacle 36 and the liner 52, the liner and filters will collapse toward the position illustrated in FIG. 5. Accordingly, the blood will be urged through the filter units 63 and expelled through the valve 58.

Figure 6:
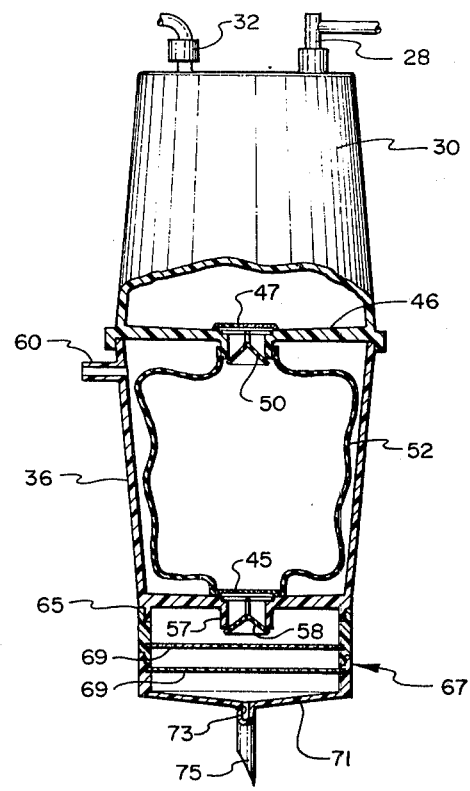
FIG. 6 is a cross-sectional view of another preferred embodiment of the invention illustrating the filter assembly removably connected to the blood receptacle.

Attention is now directed to the embodiment of FIG. 6. The embodiment of FIG. 6 differs from the aforementioned embodiments principally in that the flexible liner 52 carries no internal filter with the exception of the filter plate 45 located immediately above the valve 58. The bottom of the second receptacle 36 comprises an annular skirt 65 onto which filter assembly 67 is removably mounted. The filter assembly 67 is constructed in the form of a cylindrical cannister having filter elements 69 situated coaxially therein. The bottom 71 of the assembly 67 tapers toward the center and converges into an annular channel 73 which emerges at the tip of spike 75.

In the operation of the embodiment of FIG. 6, the liner 52 is inflated with blood as air is evacuated from between the second receptacle 36 and the liner 52, the blood passing through the unidirectional valve 50 into the liner 52. When positive pressure is communicated between the liner 52 and the receptacle 36, the liner 52 will collapse thereby expelling blood from the liner 52 through the valve 58, the positive pressure exerted on the blood urging the blood through the filter units 69 and out through the spike 75.

One significant advantage of the embodiment of FIG. 6 relates to the facility with which the particular filter units 69 may be exchanged. For example, filter media particularly effective in removing contaminants resulting from rupture of the gastrointestinal tract may be selected when an abdominal injury or the like occurs. Alternatively, the filter asembly 67 may be exchanged to provide filters particularly suited to remove bone fragments, fat particles or any other suspected blood contaminant as may be desired. In the embodiment illustrated in FIG. 6, the filter assembly 67 is threadedly attached to the second receptacle 36. Clearly, any suitable attachment technique including press-fit and snap-attachment could be used.

The Method

The method of the present invention may be practiced in two related ways as represented by FIGS. 1 and 7. In both embodiments, the blood aspirated from the patient 22 is conducted through a sterile, closed extracorporeal blood circuit. In FIGS. 2–5, the blood is aspirated at the wand 24, conducted through the tube 26 and deposited in the first receptacle 30.

The infusion set 39 may be connected by venipuncture or the like into the cardiovascular system of the patient 22 or to a transfer bag 38. The space between the liner 52 and the receptacle 36 is evacuated to expand the liner 52 and fill the liner with blood. As the liner 52 is expanded, blood will be unidirectionally transferred from receptacle 30 through the valve 50 into the liner 52. Positive fluid pressure is then communicated through the port 60 between the liner 52 and the second receptacle 36 to cause blood in the second receptacle 30 to be expelled from the liner 52 into the patient 22 or transfer bag 38. Valve 50 prevents retrograde flow into the first receptacle.

Clearly, successive collapse and recovery of the liner 52 and second receptacle caused by alternately decreasing and increasing fluid pressure between the liner 52 and receptacle 36 will urge the blood through the filter units 61, 63 and/or 69 thereby forcibly overcoming air lock and stagnation. Thus, the blood will be delivered to the patient in a significantly uncontaminated form without interfering with the ability of the wand 24 and receptacle 30 to collect blood. The extracorporeal blood system is sterile and over transfusion is significantly reduced inasmuch as the only blood conducted back to the patient is that which was taken out. Hemodilution resulting from contributions of anticoagulant and the like is minimal.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An autologous transfusion system comprising in combination:
   means for aspirating blood from a patient;
   a first blood-receiving receptacle comprising means connected to the aspirating means for conducting blood from a patient to the interior of the first receptacle, means for imposing a negative pressure within the first receptacle of sufficient magnitude to accommodate aspiration of blood through the aspirating means;
   a second blood-receiving receptacle connected to the first by a hollow conduit which communicates the interior of the second receptacle with the interior of the first and means for unidirectionally controlling blood flow from the first to the second receptacle;
   means for reducing the fluid pressure in the second receptacle below the fluid pressure in the first receptacle so as to transfer blood from the first receptacle to the second receptacle;
   a blood transfer bag communicating witht the second receptacle so that a blood flow path from the second receptacle to the blood transfer bag is formed;
   a filter cartridge comprising at least one filter transecting the blood flow path, said cartridge being interposed between the blood transfer bag and the second receptacle; and
   means for delivering positive fluid pressure greater than atmospheric to the second receptacle of sufficient magnitude to forcibly expel the blood from the second receptacle through the filter and into the blood transfer bag without interrupting the negative pressure in the first receptacle.

2. An autologous transfusion system as defined in claim 1 wherein said filter cartridge comprises:
   a housing having a blood flow path therethrough and a plurality of filter elements situated in the blood flow path;
   means for mounting the filter cartridge upon the second receptacle and in fluid communication therewith; and
   means for removably connecting a blood transfer bag into the blood flow path such that the blood forced through the filter is deposited within the transfer bag.

3. An autologous transfusion system comprising in combination:
   means for aspirating blood from a patient;
   a first blood-receiving receptacle comprising means connected to the aspirating means for conducting blood from a patient to the interior of the first receptacle, means for imposing a negative pressure within the first receptacle of sufficient magnitude to accommodate aspiration of blood through the aspirating means;
   a second blood-receiving receptacle connected to the first by a hollow conduit which communicates the interior of the second receptacle with the interior of the first receptacle;
   an infusion set communicating with the second receptacle so that a closed pathway from the interior of the second receptacle to a patient through the infusion set is formed; a filter cartridge comprising a housing mounted directly upon the second receptacle and comprising at least one filter transecting the pathway, said cartridge being interposed between the second receptacle and the infusion set; and
   means for alternately decreasing and increasing fluid pressure in the second receptacle so as to alternately (a) transfer blood from the first receptacle to the second when the fluid pressure in the second receptacle is low with respect to the fluid pressure in the first receptacle and (b) transfer blood from the second receptacle to the patient by forcibly urging the blood from the second receptacle through the filter cartridge and infusion set at a pressure greater than atmospheric when the fluid pressure in the second receptacle is high in relation to the pressure in the first receptacle, both of said blood transfers being effected without interrupting the negative pressure within the first receptacle.

4. An autologous blood transfusion system comprising in combination:
   a first rigid blood-receiving receptacle comprising means for receiving blood from a patient and means for imposing a negative pressure within the first receptacle to thereby urge blood from the receiving means to the first receptacle;
   a second rigid receptacle, flexible liner normally mounted within the second receptacle and means accommodating unidirectional blood flow from the first receptacle to the interior of the liner, the liner further comprising a blood outlet means through which blood within the liner may be expelled;
   at least one filter transecting the flexible liner; and
   means for alternately communicating negative and positive fluid pressure between the flexible liner and the rigid receptacle to (1) control the flow of blood into the liner from the first receptacle, and (2) force the blood through the filter and out of the liner through the expelling means.

5. An autologous blood transfusion system as defined in claim 4 wherein said filter comprises a flexible fabric mounted upon the internal periphery of the liner.

6. An autologous blood transfusion system as defined in claim 5 wherein said filter is oriented to intersect the blood flow path at an angle other than 90°.

7. An autologous transfusion system comprising in combination:
   a first receptacle comprising means for receiving blood from a patient, means for developing a first negative pressure in the first receptacle so as to draw blood from the receiving means into the first receptacle;
   a second receptacle and a flexible blood-receiving bag normally situated within the second receptacle and comprising means for selectively unidirectionally communicating blood to the flexible bag from the interior of the first receptacle;
   means for developing a second negative pressure by decreasing fluid pressure between the flexible blood-receiving bag and the second receptacle below the first negative pressure in the first receptacle to draw blood from the first receptacle into the flexible bag without interrupting the first negative pressure in the first receptacle;
   a filter assembly transecting the blood flow path downstream from the first receptacle; and means for communicating blood out of the flexible bag and means for increasing the fluid pressure between the second receptacle and the flexible bag to force blood through the filter assembly.

8. An autologous transfusion system as defined in claim 7 wherein said filter comprises a particle attraction filter selected to remove contaminants from the blood.

9. An autologous transfusion system as defined in claim 7 wherein said filter comprises a close mesh screen, the mesh size of the screen being selected to remove particulate matter from the blood.

10. A method of collecting blood from a patient and infusing the same blood back into the patient through a closed extracorporeal blood circuit comprising a blood aspiration device, a first receptacle, a second receptacle, a flexible liner within the second receptacle, and a filter assembly, the method comprising the steps of:

creating suction within the blood aspiration device by developing a negative pressure in the first receptacle and selectively aspirating blood from the patient through the blood aspiration device;

depositing the blood in the first receptacle;

transferring the blood from the first to the second receptacle by reducing the fluid pressure between the second receptacle and the liner below the negative pressure in the first receptacle;

thereafter increasing the fluid pressure between the liner and the second receptacle so as to urge the blood in the second receptacle through the filter assembly without interrupting the negative pressure in the first receptacle.

11. A method as defined in claim 10 further comprising selecting a filter capable of removing anticipated contaminants from the blood and placing said filter into the blood circuit.

12. A method of infusing autologous blood into a patient through an extracorporeal blood circuit having a first receptacle and a second receptacle, the second receptacle having a flexible liner therein, and at least one filter transecting the blood circuit, the method comprising the steps of:

creating a negative pressure within the first receptacle and selectively delivering blood from the patient into the first receptacle;

overcoming the negative pressure in the first receptacle by decreasing the pressure between the second receptacle and the liner below the pressure in the first receptacle to thereby transfer the blood into the second receptacle from the first without interrupting the negative pressure in the first receptacle;

expelling the blood from the second receptacle while essentially concurrently urging the blood through the filter by creating positive fluid pressure between the liner and the second receptacle; and alternately decreasing and increasing the pressure between the liner and the second receptacle thereby developing a pulsatile blood flow through the filter.

* * * * *